United States Patent [19]

Ashani et al.

[11] 4,112,082
[45] Sep. 5, 1978

[54] PHARMACEUTICAL COMPOSITION FOR TREATING GLAUCOMA AND COMPOUND 1,3,2-DIOXAPHOSPHERINGNES

[75] Inventors: Yacov Ashani, Rishon Lezion; Gavriel Amitai, Tel-Aviv; Yona Grunfeld, Rehovot; Asher Kalir; Sasson Cohen, both of Tel-Aviv, all of Israel

[73] Assignee: The State of Israel, Prime Minister's Office, The Israel Institute for Biological Research, Ness-Ziona, Israel

[21] Appl. No.: 627,387

[22] Filed: Oct. 30, 1975

[51] Int. Cl.$^2$ ............................ A01N 9/36; C07F 9/21
[52] U.S. Cl. .................................... 424/209; 260/937; 260/973
[58] Field of Search ..................... 260/937; 424/209

[56] References Cited
U.S. PATENT DOCUMENTS

| | | | |
|---|---|---|---|
| 3,159,664 | 12/1964 | Bartlett | 260/937 |
| 3,286,001 | 11/1966 | Buchner et al. | 260/937 X |

Primary Examiner—Anton H. Sutto

Attorney, Agent, or Firm—Browdy & Neimark

[57] ABSTRACT

Organo-phosphorus compounds of the general formula

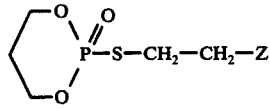

wherein Z is a member selected from

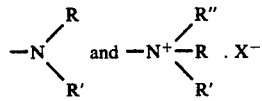

wherein R and R' are each selected from hydrogen and lower alkyl, R" designates a member selected from methyl and ethyl, and X$^-$ is an anion may be used as active ingredient in pharmaceutical and pesticidal, especially acaricidal and fungicidal, compositions of matter of low mammalian toxicity.

9 Claims, No Drawings

PHARMACEUTICAL COMPOSITION FOR TREATING GLAUCOMA AND COMPOUND 1,3,2-DIOXAPHOSPHERINGNES

BACKGROUND OF THE INVENTION

Anticholinesterase agents are used as topical agents for the treatment of ophthalmological conditions such as glaucoma; of certain muscle disorders, such as myasthenia gravis and as insecticides. For example, DFP (diisopropyl-phosphorofluoridate) and O,O-diethyl-S-(2-(N,N,N-trimethylammonio)ethyl)-phosphorothiolate iodide (Phospholine) are used for the relief of intraoccular pressure in glaucoma. Tetram (O,O-diethyl S-(2-(N,N-diethylamino)ethyl)-phosphorothiolate is known as powerful insecticide. Carbamates such as physostygmine and pyridostigmine are useful in the treatment of myasthenia gravis, (Flake New Eng. J.Med.288, 27 (1973)).

All the above compounds have the drawback of having a comparatively high toxicity towards mammals. Furthermore, some of the compounds used as drugs have a comparatively brief duration of activity, and this is especially pronounced with the carbamates. The side-effects inherent to such active anticholinesterase (AcChE) inhibitors reduces their wide applicability.

The $LD_{50}$ of phospholine to mice is about 0.13 mg/kg (s.c.) and that of neostigmine is 0.42 mg/kg (mice s.c.). DFP is somewhat less toxic, the $LD_{50}$ towards mice i.p., being 4 mg/kg. It has been shown recently that AcChE inhibited by 1,3,2-dioxaphosphorinane-2-oxide derivatives of the formula

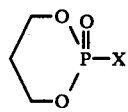

wherein X designates —F, —Cl or p-nitrophenyl, undergoes spontaneous reactivation with $t_{1/2} = 12$ minutes at pH 7.0 (Ashani et al, Biochem.11, 3518 (1972)). These compounds are characterized by a low toxicity towards mammals, this being above 100 mg/kg for mice, s.c. It has also been established that phosphorothiolates with leaving groups of the formula (alkyl)$_2$—N—CH$_2$—CH$_2$S— ae excellent inhibitors of AcChE, (Maglothin et al, Biochem.,13, 3520 (1974)).

SUMMARY OF THE PRESENT INVENTION

The present invention relates to novel compounds of the general formula

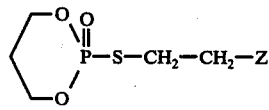

wherein Z designates

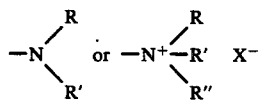

where R and R' designate lower alkyl of 1 to 4 carbon atoms or hydrogen, and where R" designates —H, methyl or ethyl, and wherein $X^-$ designates an anion, which in the case of compounds to be used as drugs must be physiologically acceptable. Suitable anions are $I^-$, $CH_3SO_3^-$, $Cl^-$, $Br^-$, $NO_3^-$ and the like. Amongst suitable alkyls (R and R') there may be mentioned methyl, ethyl, propyl, isopropyl, butyl, isobutyl, tert-butyl.

More specifically, the invention relates to compounds of the formulas

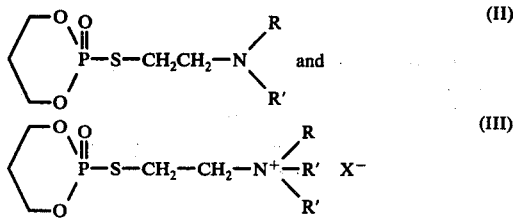

wherein R, R' and R" and X are as defined above, and to pharmaceutical and insecticidal compositions of matter containing these as active ingredients.

The novel compounds are effective AcChE inhibitors, and they are characterized by a lower toxicity of mammals. They can be used effectively for the treatment of glaucoma and for the treatment of other conditions where cholinergic functions are impaired, such as myasthenia gravis. The compounds of the present invention can be used for these applications in the form of conventional ophthalnological compositions of matter, in suitable carriers or buffers, and for the other purposes in a manner similar to that used hitherto with other AcChE inhibitors.

The novel compounds are also valuable insecticidal agents, and they are especially suited for the control and eradication of pests such as mites and the like. They are advantageously used with suitable carriers, diluents and the like, in the form of conventional insecticidal formulations. They may be used with adjuvants such as penetrating agents, surface active agents and the like. They may be used in the form of liquid formulations for spraying or aerosolization; they may be used in the form of wettable powders or in the form of dusts and the like.

The present invention also relates to a process for the production of the novel compounds of the present invention. Compounds of the formula II can be prepared by various routes, such as, for example:

a. The reaction of N,N-dialkylaminoethanol (Na salt) with 2-chloro-1,3,2-dioxaphosphorinane-2-sulfide in a dry solvent such as benzene, toluene, etc. under reflux conditions for a number of hours.

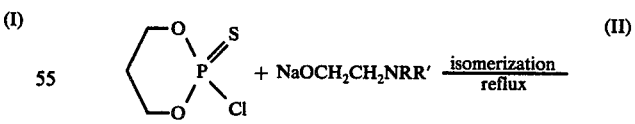

b. By reacting N,N-dialkylaminoethyl chloride with the sodium salt of 2-thiolo-1,3,2-dioxaphosphorinane 2-oxide under reflux in a dry solvent (benzene, ether, acetone, etc.)

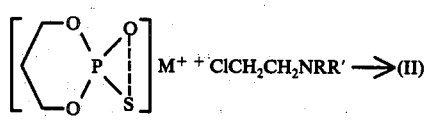

c. By reacting N,N-dialkylaminoethylmercaptan (Na salt) and 2-chloro-1,3,2-dioxaphosphorinane-2-oxide in refluxed dry solvent such as ether in an inert atmosphere.

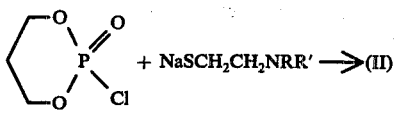 + NaSCH$_2$CH$_2$NRR' → (II)

d. Compounds of Formula (III) are prepared by reacting a compound of Formula (II) with a compound R"X, where R" and X are alkyl and anion respectively as defined above. The reaction is affected by mixing the corresponding II analog with an alkylhalide (R"X) in a dry solvent such as acetone or ether at room temperature.

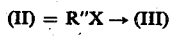

Compounds of the general formulas II and III defined above were prepared and IR and NMR spectral data are in good agreement with the structures of II and III, respectively. The preparation of compound of the invention is illustrated by way of illustration only by the following examples.

EXAMPLE 1

2-S-(2'-(N,N-diethylamino)ethyl)thio-1,3,2-dioxaphosphorinane-2-oxide ((II), R and R' = C$_2$H$_5$)

Route a

Small pieces of Na (4.6 g., 0.2 moles) were added to a solution of diethylaminoethanol (26.7 g, 0.3 moles) in dry benzene (300 ml.) and heated until the metal is completely dissolved. The mixture was stirred and cooled to room temperature with continuous stirring. 2-chloro-1,3,2-dioxaphosphorinane-2-sulfide (J. Ziemlanski and W.P. Kalachnikov, Zh.Obsch.Khim.,37, 1141 (1967)) (34.5g., 0.2 moles) was added in portions. The mixture was refluxed for 5 hours and allowed to stand overnight with continuous stirring at room temperature. The white precipitate was filtered off and the solvent was removed in vacuo (20 mm mercury). The crude oil was dissolved in benzene (100 ml) and washed with water (2 × 50 ml.) The benzene solution was dried over MgSO$_4$ and the solvent removed under reduced pressure (last traces at 0.05 mm). The residual yellow oil (40 g. 79%) was distilled at 4 × 10$^{-5}$ mm Hg and 63° C. to yield a colorless liquid (5g. 10%). The distilled product was checked by GC (glass column, 0.3 × 1.8 m) 10% silicone oil DC-550 on chromosorb WAW DMCS 80/100 mesh, temp. of inject. 200° C., column: 190° C., detector: 200° C., with nitrogen as a carrier gas (35 ml/min) and found to be a single component.

| % calcd.: | C 42.69; H 7.90 ; N 5.53; P 12.25 |
| % Found : | C 42.10; H 7.85 ; N 6.34; P 11.41 |

Route b

N,N-diethylaminoethylchloride was added dropwise into a heterogeneous mixture of the sodium salt of 2-thiolo-1,3,2-dioxaphosphorinane-2-oxide, in dry benzene (400 ml). The mixture was refluxed 2.5 hours and cooled to room temperature. A white precipitate was formed and filtered off. The benzene was removed in vacuo (20 mm) to afford a pale yellow oil (27 g. 30%). The oil was purified by column chromatography. A glass column was packed with Merck Kieselgel 60 (80 cm. height, 5 cm i.d.) in a mixture of acetone:benzene:methanol (5:4:1 respectively) which was also used as the eluant. The separated compound was checked for purity on silica gel chromatoplates (chloroform:methanol 9:1, R$_f$ = 0.40, acetone:benzene:methanol, 5:4:1 R$_f$ = 0.70).

EXAMPLE 2

2-S-(2'(N,N,N-diethylmethylammonio)ethyl)thio-1,3,2-dioxaphosphorinane-2-oxide methanesulfonate (III,R,R' = C$_2$H$_5$, R"=CH$_3$, X=CH$_3$SO$_3$−)

(4.2 g., 0.011 mole) was dissolved in dry benzene (30 ml) and methylmethanesulfonate was added in excess. The mixture was refluxed for 2 hours to yield a brown oily precipitate. After decanting most of the mother liquid and allowing to stand overnight a yellowish solid was obtained. The product was triturated with dry acetone (3×10 ml) and dried over P$_2$O$_5$ in vacuo (20 mm Hg) at 45° C. for 3 hours m.p. 97°–98° C.

| % Calcd: | C 36.36 H 7.16 N 3.86 P 8.54 |
| % Found: | C 36.18 H 7.18 N 4.07 P 8.56 |

Some of the physical and biological data representative of members of the novel series are summarized in Table I.

TABLE I

Physical, biochemical and toxicological data for the new compounds related to formulae VII and VIII.

| No. of Comp. | R,R' | R" | X | m.p. or b.p. (mm Hg)° C. | K$^a$$_{(M)}$ | k'$_{(min-1)}$ | k'/K (M$^{-1}$min$^{-1}$) | LD$_{50}$ to mice s.c. mg/Kg. |
|---|---|---|---|---|---|---|---|---|
| II(A)$^b$ | CH$_3$ | — | — | — | — | — | — | — |
| II(B) | C$_2$H$_5$ | — | — | 63° C(4×10$^{-5}$) | 5.0×10$^{-4}$ | 2.08 | 4.1×10$^3$ | 700 |
| II(C) | i-C$_3$H$_7$ | — | — | C | 1.2×10$^{-2}$ | 0.31 | 25.0 | 550 |
| III(A) | CH$_3$ | CH$_3$ | CH$_3$SO$_3$− | 143–6 | 3.3×10$^{-3}$ | 2.5 | 0.8×10$^3$ | 190 |
| III(B) | C$_2$H$_5$ | CH$_3$ | CH$_3$SO$_3$− | 97–8 | 1.4×10$^{-3}$ | 1.61 | 1.1×10$^3$ | 370 |
| III(C) | i-C$_3$H$_7$ | CH$_3$ | I− | 88–90° | — | — | — | 230 |

$^a$The kinetic parameters K., k', k$_s$ and k'/K (the bimolecular rate constant) refer to the following scheme =

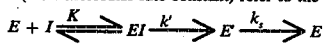

where E, I, EI and E' represent the free enzyme the inhibitor, the reversible complex between the enzyme and inhibitor and the inhibited enzyme, respectively.
$^b$A very unstable compound which is converted rapidly to the corresponding piperazinium salt.
$^c$Viscous oil purified by column chromatography.

BIOLOGICAL ACTIVITY: (See Table 1)

All the novel compounds related to this invention were found to act as moderate inhibitors of acetylcholinesterase. Comparison of the new series with the highly toxic open chain analogs (e.g. phospholine, tetram) indicates clearly that the low toxicity of the novel compounds can be ascribed to the difference in the bimolecular rate constant of the phosphorylation (k'/K) and the spontaneous reactivities (ks). For example, cpd II(B) was injected intravenously (1 mg/kg) to beagle dogs. No discernible signs of intoxications were observed during the experiment. Blood cholinesterase reduced to 37–39% of the original activity after 5 hours and remained at this level throughout the next 24 hours. This can be ascribed to the slow elimination rate of compound II(B) (and probably other members of this series) from body compartments. A pilot clinical trial in a patient with aphakic glaucoma showed superiority of II(B) over phospholine. Thus, treatment of a twice daily application with one drop of 0.15% solution of II(B) lowered intraocular pressure from 36 to 20 mmHg within 9 days. Using phospholine under the same treatment regime, it required 30 days of consecutive treatment to reduce intraocular pressure from 40 to only 24 mmHg.

INSECTICIDAL ACTIVITY

The novel compounds of the present invention of Formulas II and III respectively, were tested in order to determine their efficacy as insecticides, and this in view of the comparatively very low toxicity of same to mammals, compared with other insecticidally active organophosphorus compounds. The compounds were compared with other organophosphorus insecticides, such as malathion.

A compound of Formula II, where R and R' are —$C_2H_5$ was tested as acaricide against spider mites (Tetrantychus strain). The following results were obtained:

| Compound: | Normal Strain $LD_{50}, \mu g/8\ cm^2$ | Resistant Strain $LD_{50}, \mu g/8\ cm^{2*}$ |
|---|---|---|
| II,R,R"=$C_2H_5$ | 35 | 40 |
| malathion | 50 | 40 |

The effectivity is slightly better than that of malathion, whereas the mammalian toxicity is in the same range.

The compound 2-S-[2'-(N,N-diethylamino)ethyl]thio-1,3,2-dioxaphosphorinane-2-oxide was found to be an effective antimycotic agent. It was mixed in a 50/50 weight ratio with polyethyleneglycol 400, which latter has no such activity. This formulation was found to be effective against:
 *Candida albicans*
 *Cryptococcus neoformans*
 *Aspergillus fumigatus*
 *Phialophora pedrosoii*
 *Penicillium sp.*

We claim:
1. A compound of the formula

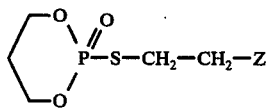

wherein Z designated a group -NRR' or -$N^+$RR'R".$X^-$, where R designates hydrogen or lower alkyl of up to, and including, 4 carbon atoms R' designates lower alkyl of up to, and including, 4 carbon atoms, and R" designates hydrogen, methyl or ethyl, and where $X^-$ is a physiologically acceptable anion.

2. A pharmaceutical composition for treating glaucoma, comprising a compound in accordance with claim 1 and a pharmaceutically acceptable carrier, said compound being present in an amount effective for the treatment of glaucoma.

3. A method of using the composition of claim 2 comprising administering said composition to the eye of mammals having glaucoma in an amount sufficient to treat the glaucoma, wherein said pharmaceutically acceptable carrier is an ophthalmological carrier.

4. A compound according to claim 1, of the formula

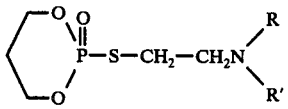

wherein R and R' are as defined in claim 1.

5. A compound according to claim 1, of the formula

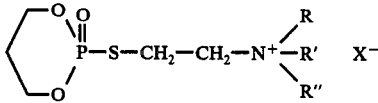

wherein R, R', R" and $X^-$ are as defined in claim 1.

6. A compound according to claim 4, wherein R and R' are ethyl.

7. A compound according to claim 5 wherein R and R' are both ethyl, R" is methyl and $X^-$ is a methanesulfonate anion.

8. A compound in accordance with claim 1 wherein X is selected from methane sulfonyl, iodide and nitrate.

9. A pharmaceutical composition in accordance with claim 2 wherein said pharmaceutically acceptable carrier is in a form suitable for ophthalnological application.

* * * * *